US006919954B2

(12) United States Patent
Sasaki et al.

(10) Patent No.: US 6,919,954 B2
(45) Date of Patent: Jul. 19, 2005

(54) METHOD AND APPARATUS FOR MEASURING INTERNAL INDEX OF REFRACTION OF PREFORM OF OPTICAL FIBER

(75) Inventors: Issei Sasaki, 2-7, Maeda 9-jo 17-Chome, Teine-Ku, Sapporo-shi (JP); Fujio Kato, Sapporo (JP)

(73) Assignees: Issei Sasaki, Sapporo (JP); Advanced Technology, Inc., Sapporo (JP)

( * ) Notice: Subject to any disclaimer, the term of this patent is extended or adjusted under 35 U.S.C. 154(b) by 0 days.

(21) Appl. No.: 10/149,413

(22) PCT Filed: Jun. 12, 2001

(86) PCT No.: PCT/JP01/04951
§ 371 (c)(1),
(2), (4) Date: Jun. 20, 2002

(87) PCT Pub. No.: WO02/35201
PCT Pub. Date: May 2, 2002

(65) Prior Publication Data
US 2002/0180958 A1 Dec. 5, 2002

(30) Foreign Application Priority Data
Oct. 20, 2000 (JP) ........................................ 2000-320497

(51) Int. Cl.[7] .............................................. G01N 21/00
(52) U.S. Cl. ...................................... 356/128; 356/73.1
(58) Field of Search ................................ 356/128–133, 356/73.1; 385/12–14

(56) References Cited
U.S. PATENT DOCUMENTS

| | | | | |
|---|---|---|---|---|
| 4,181,433 A | * | 1/1980 | Marcuse | 356/73.1 |
| 4,227,806 A | * | 10/1980 | Watkins | 356/73.1 |
| 4,515,475 A | * | 5/1985 | Payne et al. | 356/73.1 |
| 4,519,704 A | * | 5/1985 | Mansfield et al. | 356/73.1 |
| 4,744,654 A | * | 5/1988 | Jinno et al. | 356/73.1 |
| 4,776,667 A | * | 10/1988 | Yoshida et al. | 385/119 |
| 5,078,488 A | * | 1/1992 | Yamaguchi et al. | 356/73.1 |
| 5,365,329 A | * | 11/1994 | Svendsen | 356/73.1 |
| 5,396,323 A | * | 3/1995 | Abbott et al. | 356/73.1 |
| 5,633,708 A | * | 5/1997 | Svendsen | 356/73.1 |
| 6,538,755 B1 | * | 3/2003 | Propst, Jr. | 356/635 |
| 6,611,321 B1 | * | 8/2003 | Sasaki | 356/73.1 |

FOREIGN PATENT DOCUMENTS

| | | | |
|---|---|---|---|
| JP | 357042835 | * | 3/1982 |
| JP | 401311245 A | * | 12/1989 |
| JP | 404095848 | * | 3/1992 |

* cited by examiner

Primary Examiner—Hoa Q. Pham
(74) Attorney, Agent, or Firm—Westerman, Hattori, Daniels & Adrian, LLP

(57) ABSTRACT

The invention relates to a method and system for measuring the internal refractive index of an optical fiber preform with high precision. The internal refractive index of an optical fiber preform (2) is measured from the state of bending of a light ray (4) passing across the optical fiber preform (2), so that the refractive index distribution of the optical fiber preform (2) is found on the basis of the angle of bending of the light ray calculated from a specific relation between a light ray start position (8) and a light ray detection position (9). The surface of a light source (1) is scanned by a knife-edge (6) and the light ray start position (8) on the light source is determined depending on the interception of the light ray (4) by the knife-edge (6) or the de-interception of the light ray, thereby learning the start position (8) of the detected light ray (4) on the light source (1).

7 Claims, 5 Drawing Sheets

101: optical fiber preform
102: CRT light source surface
103: CCD camera
104: light source
105: image signal
106: index-matching solution
107: computer
108: knife-edge image
109: light ray start position
110: driving program 1: planar light source
2: optical fiber preform
3: CCD device
4: light ray
5: phototaking lens
6: movable knife-edge
8: light ray start position
9: light ray arrival position 10 : CRT (light source)
11 : computer
12 : display device for computer (10 : CRT)
13 : knife-edge image
14 : driving program
16 : light ray arrival position
17 : edge position
18 : light ray start position 101: optical fiber preform
102: CRT light source surface
103: CCD camera
104: light source
105: image signal 106: index-matching solution
107: computer
108: knife-edge image
109: light ray start position
110: driving program

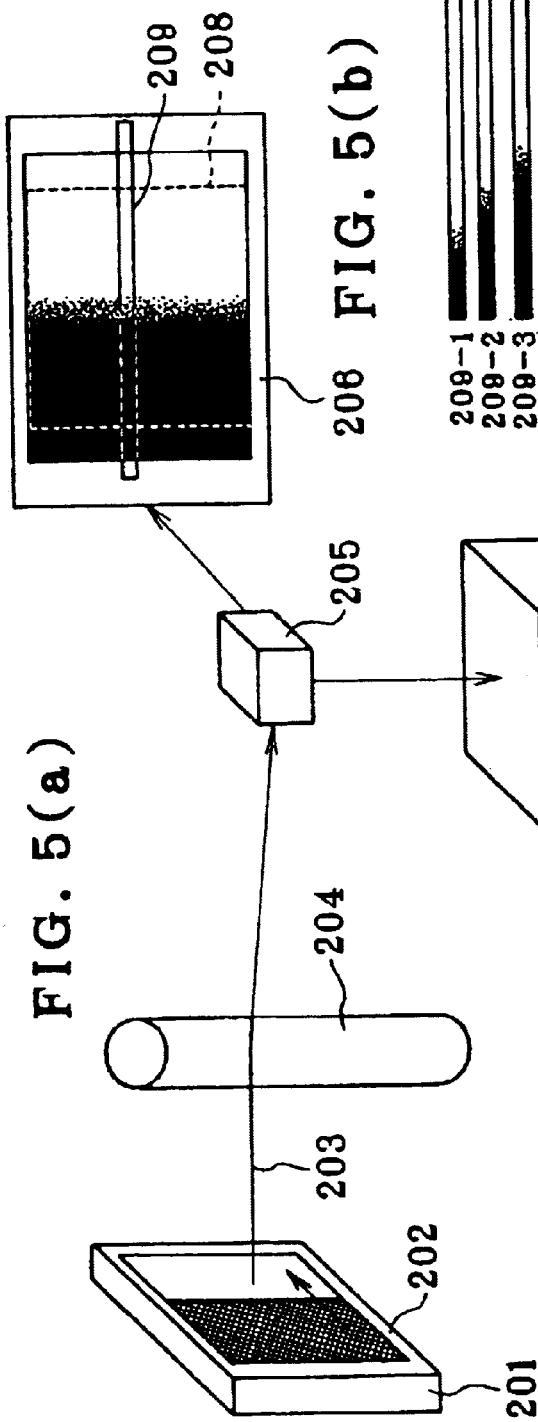
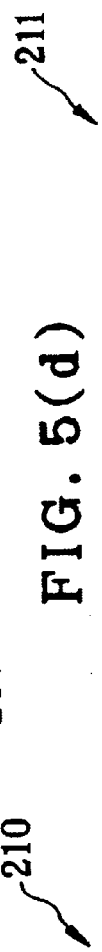
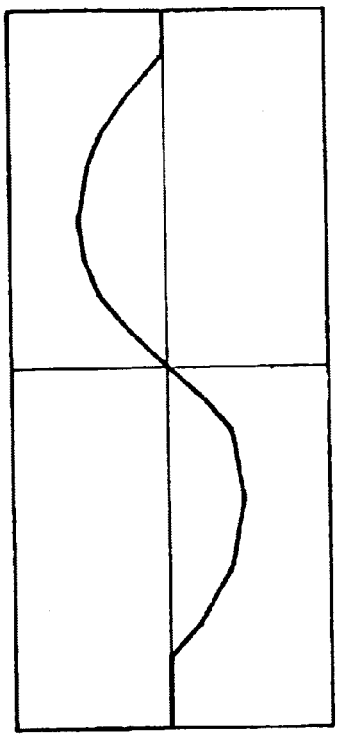

METHOD AND APPARATUS FOR MEASURING INTERNAL INDEX OF REFRACTION OF PREFORM OF OPTICAL FIBER

ART FIELD

The present invention relates to a method and system for measuring the internal refractive index of optical fiber preforms.

BACKGROUND ART

Optical fibers are fabricated by heating and softening the end of a glass rod form of intermediate products called preforms, and drawing the same. At this time, the internal refractive index structure required for an optical fiber is formed on the preform stage, and the performance of the optical fiber to be fabricated is determined by whether this structure is acceptable or not. Of importance to this end is precise control of refractive index profiles at an optical fiber fabrication step, and measurement for checking the same. As the precision of the measuring instrument used for this measurement becomes worse, the fabricating yield of optical fibers becomes low and the cost of optical fibers is adversely affected.

The determination of the internal structure of an optical fiber perform has so far been made using the bending of light rays traversing the interior of the perform, as set forth in I. Sasaki, D. N. Payne and M. J. Adams: "Measurement of refractive index profiles in optical fiber performs by spatial filtering technique", Electronics Letters, 16, 6, pp. 219–221.1980–03.

When parallel rays are used, their bending is measured upon traversing the preform, and with a method making use of image distortions (U.S. Pat. No. 3,072,986), the bending or inflection is determined from the angle of incidence. The latter has a feature of being more compatible with a wider range of performs as compared with the former.

In the latter method, an image is located behind a columnar form of optical fiber preform having an uneven refracting index distribution therein. Used for the image is a pattern wherein a light ray starting from one point on an image carries information on positions within that image. A picture of that image is taken across the optical fiber preform. A distortion of the thus taken image is analyzed to find a deflection function, on the basis of which the refractive index distribution of the optical fiber perform is determined.

For an actual measuring technology, however, an oblique edge image is utilized. A problem with this technology is that it is not easy to precisely measure the refractive index distribution at the plane vertical to the axis of the preform. It follows that there is a problem in connection with a preform having a refractive index profile fluctuating in the axial direction.

DISCLOSURE OF THE INVENTION

The state of the prior art being like this, an object of the present invention is to provide a method and system for measuring the internal refractive index of an optical fiber preform with high accuracy.

According to the first aspect of the invention, this object is achievable by the provision of a method for measuring the internal refractive index of an optical fiber preform from a state of bending of a light ray passing across the optical fiber preform, in which the refractive index distribution of the optical fiber preform is found on the basis of the angle of bending of the light ray calculated from a specific relation between a light ray start position and a light ray detection position, characterized in that the surface of a light source is scanned by a knife-edge and the light ray start position on the light source is determined depending on the interception of the light ray by the knife-edge or the de-interception of the light ray, thereby learning the start position of the detected light ray on the light source.

In one embodiment of this aspect, the knife-edge passing across the optical fiber preform is phototaken to extract a portion of the thus phototaken knife-edge image corresponding to the position of the section of the optical fiber preform to be measured, which is vertical to a specific axis thereof, so that portions of the phototaken image are combined into one single image as a function of the knife-edge position or as a function of time when the knife-edge is moved at a constant speed, and the combined image is analyzed to find the angle of bending of the light ray from a geometrical relation between the light ray start position and detection position.

In another embodiment of the first aspect, a self-emission type image display device is used as the light source, so that the shape of the knife-edge is displayed on the screen of the display device to form a scanning moving image, thereby determining the light ray start position.

It is here noted that a CRT or a liquid crystal display device having a backlight may be used as the self-emission type image display device.

The present invention provides a system for measuring the internal refractive index of an optical fiber preform from a state of bending of a light ray passing across the optical fiber preform, in which the refractive index distribution of the optical fiber preform is found on the basis of the angle of bending of the light ray calculated from a specific relation between the start and detection positions of the light ray, characterized by comprising a planar light source, a knife-edge for scanning the front surface of the planar light source in a direction vertical to the axis of the optical fiber preform, a supporting device for supporting the optical fiber preform in front of the knife-edge, a phototaking device for phototaking an image of the planar light source scanned through the optical fiber preform, and a processing device for calculating the angle of bending of the light ray from a position at which the light ray is intercepted by the knife-edge or a position at which the light ray is de-intercepted and a corresponding position on the image pickup plane of the phototaking device, and finding the internal refractive index of the optical fiber preform on the basis of the angle of bending.

There is also provided a system for measuring the internal refractive index of an optical fiber preform from a state of bending of a light ray passing across the optical fiber preform, in which the refractive index distribution of the optical fiber preform is found on the basis of the angle of bending of the light ray calculated from a relation between the start and detection positions of the light ray, characterized by comprising a self-emission type image display device for displaying a scanning moving image of knife-edge shape, a supporting device for supporting the optical fiber preform in front of the image display device, a phototaking device for phototaking the scanning moving image of knife-edge shape through the optical fiber preform, and a processing device for calculating the angle of bending of the light ray from a position at which the light ray is intercepted by the knife-edge or a position at which the light ray is de-intercepted and a corresponding position on the image pickup plane of the phototaking device, and finding the internal refractive index of the optical fiber preform on the basis of the angle of bending.

Preferably but not exclusively, a CRT or a liquid crystal display device having a backlight may be used as the self-emission type image display device.

In accordance with the present invention, the knife-edge is scanned on the light source surface so that the light ray start position on the light source is judged depending on the interception of the light ray by the knife-edge or the de-interception of the light ray, thereby learning the start position of the detected light ray on the light source. Even with an optical fiber preform having a refracting index profile fluctuating in the axial direction, it is thus possible to achieve precise measurement of the refractive index distribution on the plane vertical to that axis.

BRIEF DESCRIPTION OF THE DRAWINGS

FIG. 5 is illustrative of another embodiment of how to measure the internal refractive index of an optical fiber preform according to the present invention.

BEST MODE FOR CARRYING OUT THE INVENTION

Instead of the conventional method harnessing image distortions (U.S. Pat. No. 3,072,986), the present invention relies upon a method wherein a linear knife-edge is moved in the direction of bending of a light ray. That is, the knife-edge is moved to detect whether the light ray is intercepted or de-intercepted. At this point, the position of the knife-edge is recorded thereby learning the position of the light ray. This in turn enables the internal refractive index to be measured at the plane vertical to the axis of the preform, thereby providing a solution to the aforesaid problems.

Some mechanical driving mechanism is need for the scanning movement of the knife-edge on this principle. However, mechanical driving is not always practical, because scanning takes some time and so the whole measuring operation becomes redundant. Instead, self-emission type image displays such as a CRT and a two-dimensional planar liquid crystal display device having a backlight is used as a light source. This is set up as a display for a computer, on the screen of which a knife-edge is indicated. If this is constructed as a moving image traveling in any desired direction, it is then possible to obtain the same effect as is the case with the mechanical scanning of the knife-edge, so that fast scanning is possible.

The principles and embodiments of the method and system for measuring the internal refractive index of an optical fiber preform according to the present invention are now explained at great length with reference to the drawings.

Figure 1:
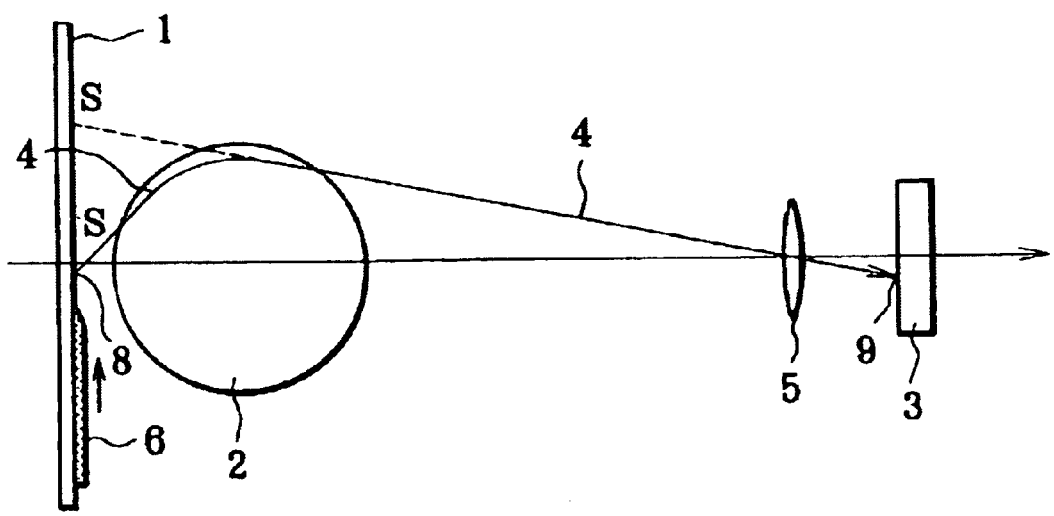
FIG. 1 is illustrative of the principles of the method and system for measuring the internal refractive index of an optical fiber preform according to the present invention.

As shown in FIG. 1 illustrative of those principles, there is a planar light source 1. Now consider the case where an optical fiber preform 2 illuminated from behind by the light source 1 is phototaken by projecting it onto a CCD device 3 through a lens 5. While the image of the preform 2 is projected on the image pickup plane of the CCD device 3, it is understood that if, on this image plane, one point 9 to be measured is bright, then a light ray 4 starts from a certain one point 8 on the light source surface, striking on the CCD device 3 through preform 2. In FIG. 1, S is a virtual start position for the light ray 4, and S' is an actual start position (8) for the light ray 4.

Next, consider the case where a knife-edge 6, positioned on the surface of the light source 1, is moved along the surface of the light source 1 (as indicated by an arrow in FIG. 1) to intercept the light ray. Then, the point 9—well lit by this time—on the CCD device 3 turns dark. The position of the knife-edge 6, where the point 9 turns dark, is indicative of the start position 8 for the light ray 4. Accordingly, if this is recorded, it is then possible to find the angle of bending of the light ray by calculation.

Referring to U.S. Pat. No. 3,072,986, if the start position for the light ray 4 is detected, all the equations set forth therein can then be calculated to determine a deflection function $\phi(y'')$. If this is converted by known mathematical operations (for instance, Electron Lett., 13, pp. 736–738 (1977); and J. Lightwave Tech., LT-3, pp. 678–683 (1985)), it is then possible to find the refractive index distribution.

Figure 2:
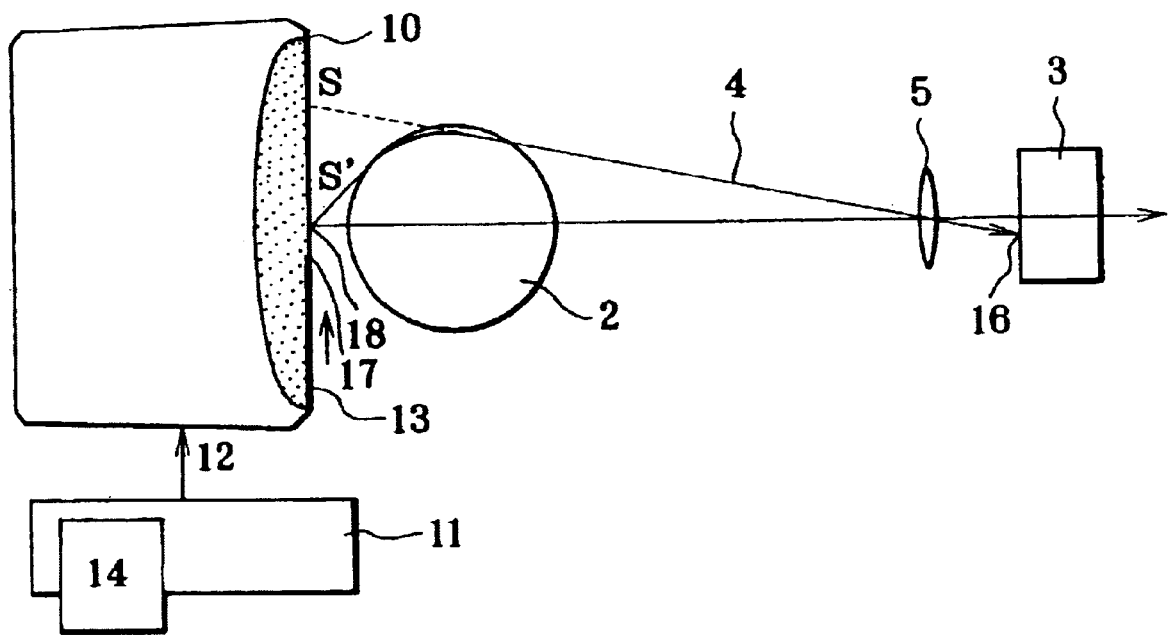
FIG. 2 is illustrative of the principle of using a CRT as a light source.

The principle of using a CRT (cathode-ray tube) as the light source is illustrated in FIG. 2. While this principle is much the same as in FIG. 1, it is understood that there is a breakthrough effect. As shown, a CRT 10 is a display 12 for a computer 11, and a knife-edge 13 on the screen of the CRT 10 is drawn by a computer program 14. Consider the case where this knife-edge 13 is moved in the form of a moving image. If the point 16 to be measured on a CCD device 3 turns dark or bright, a start position 18 for a light ray can be identified from the then position 17 of this knife-edge 13.

In this case, the principle of the present invention is achievable by pure use of software, making fast operations possible.

Figure 3:
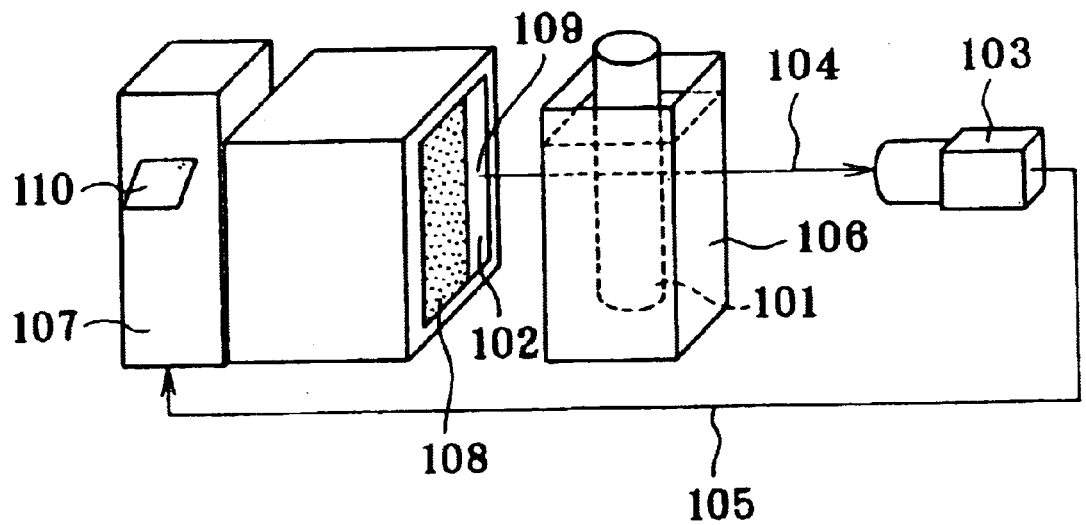
FIG. 3 is illustrative of one embodiment of the system for measuring the internal refractive index of an optical fiber preform according to the present invention.

One embodiment of the system for measuring the internal refractive index of an optical fiber preform according to the present invention is illustrated in FIG. 3. An optical fiber preform sample 101 is illuminated with light from a CRT 102 acting as a light source while immersed in an index-matching solution 106. A light ray 104 starting from the light source 102 transmits through the optical fiber preform sample 101, arriving at a CCD device in a CCD camera 103. It is here noted that the optical fiber preform sample 101 is supported by a supporting device (not shown) in a stable manner.

Drawn on the CRT 102 by a computer 107, a knife-edge 102 is designed to be moved using a program 110. An image signal 105 obtained at the CCD device in the CCD camera 103 is sent to the computer 107 to detect the interception of the light ray in association with the displacement of the knife-edge. It is here noted that reference numeral 109 is a light ray start position.

Figure 4:
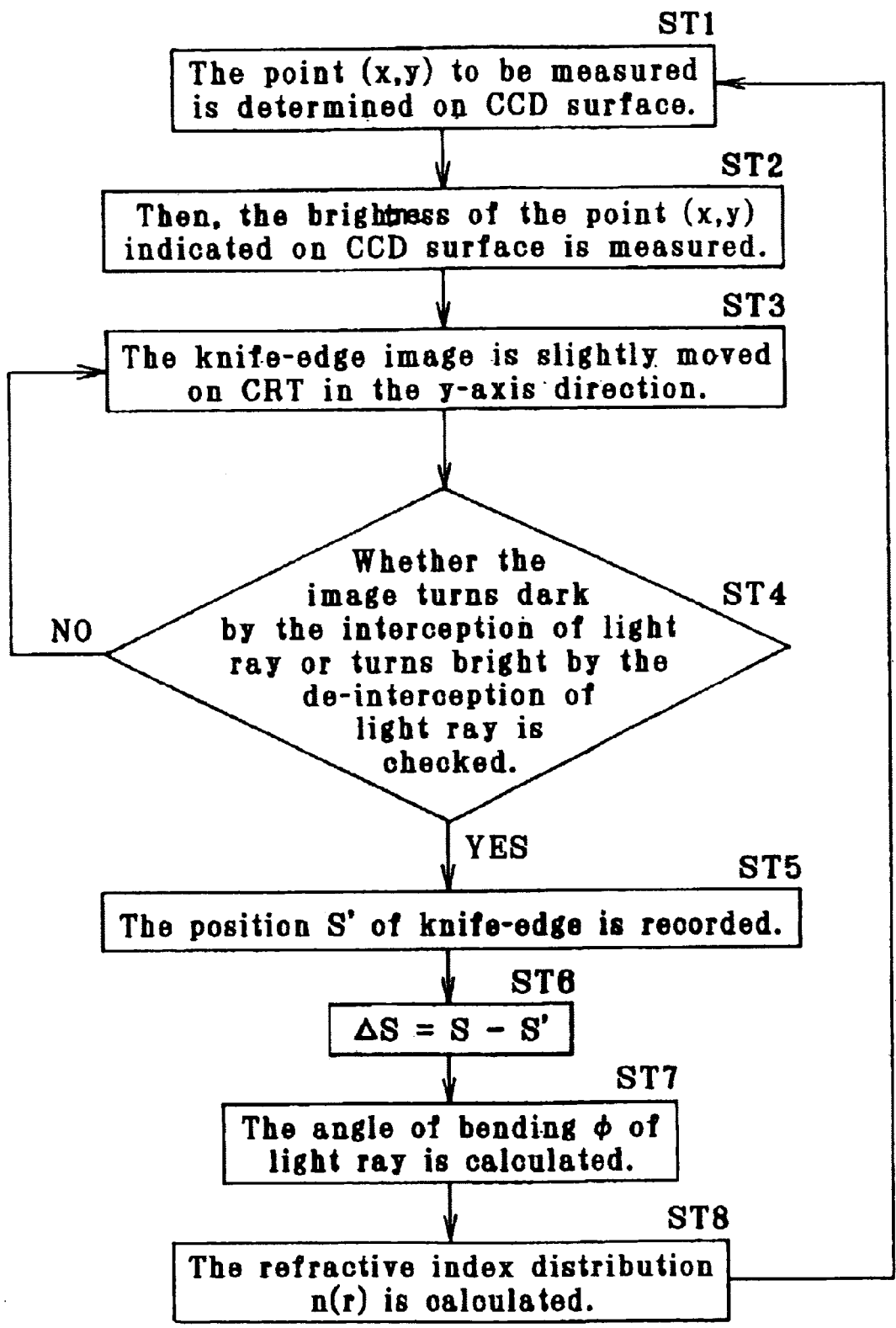
FIG. 4 is a flowchart illustrative of the operation of the system of FIG. 3.

The operation of the system is now explained with reference to the flowchart of FIG. 4.

At step ST1, the point (x, y) to be measured is first determined on the CCD surface.

Then, at step ST2 the brightness of the point (x, y) indicated on the CCD surface is measured.

At step ST3, a knife-edge image is slightly moved on a CRT in the y-axis direction (vertical to the axis of an optical fiber preform) according to a computer program. At this time, whether the image turns dark by the interception of the light ray or turns bright by the de-interception of the light ray is checked. If this does not occur, the operation at the step ST3 is repeated.

If, at step S4, the image turns dark by the interception of the light ray or turns bright by the de-interception of the light ray, the position S' of the knife-edge is recorded at step ST5. This position of the knife-edge is indicative of the light ray start point on the light source surface.

Then, at step ST6, a difference ΔS between an apparent light ray start position S at the time the knife-edge image turns dark or bright and the actual light ray start position S' is found by calculation. At step ST7, the angle of bending φ of the light ray is geometrically calculated according to the teachings of U.S. Pat. No. 3,072,986.

Then, the refractive index distribution n(r) is calculated from the angle of bending (deflection function) φ found at step ST6. Given the angle of bending φ, the refractive index distribution n(r) can be calculated, as taught in U.S. Pat. No. 3,072,986.

FIG. 5 is illustrative of another embodiment of the method for measuring the internal refractive index of an optical fiber preform according to the present invention.

As shown in FIG. 5(a), a planar liquid crystal display device 201 is used as a light source. Displayed on the display device 201, a knife-edge image 202 is moved in a direction shown by an arrow so that a light ray 203 is intercepted. At this time, the light ray 203 traverses an optical fiber preform 204, arriving at a CCD image pickup device 205 to obtain an image.

A monitor 206 connected to the CCD image pickup device 205 is provided to display the then image. That is, an image 208 of the optical fiber preform 204 having a knife-edge's shadow is projected on the monitor 206. Then, this image is captured in a computer 207 where the position of the section of the preform to be measured, for instance, a portion 209 is extracted from this image and recorded in the form of a pixel line 209-1, as shown in FIG. 5(b).

Then, the knife-edge image 202 is slightly moved in the arrow direction to record a pixel line 209-2. In this way, a series of pixel lines 209-1, 209-2, . . . are recorded until the knife-edge is successively moved across the light source surface.

Next, if a series of pixel lines are combined into one single image, it is then possible to obtain an image 210 comprising an assembly of pixel lines, as shown in FIG. 5(c). In this image 210, the ordinate provides a function with respect to the position of the knife-edge, and the light-to-shade boundary is indicative of the position at which the light ray 203 starting from the light source is intercepted. Thus, if this boundary is traced, it is then possible to obtain a function indicative of the light ray start position. If this is processed according to the image processing taught in U.S. Pat. No. 2,072,986, a light ray deflection function 11 (φ) is then obtained, as shown in FIG. 5(d).

If a self-emission type display device 201 using TFT (thin film transistor) liquid crystals is used as the light source, it is then possible to prevent interferential flickering that may otherwise be caused by a slight loss of synchronism between image scanning lines.

The method and system for measuring the internal refractive index of an optical fiber preform according to the present invention have been explained with reference to the principles and embodiments of the invention, it is understood that the invention is not limited to such embodiments and so various modifications may be possible.

POSSIBLE INDUSTRIAL APPLICATIONS

With the method and system for measuring the internal refractive index of an optical fiber preform according to the invention as can be understood from the foregoing, the knife-edge is scanned on the light source surface so that the light ray start position on the light source is judged depending on the interception of the light ray by the knife-edge or the de-interception of the light ray, thereby learning the start position of the detected light ray on the light source. Even with an optical fiber preform having a refracting index profile fluctuating in the axial direction, it is thus possible to achieve precise measurement of the refractive index distribution on the plane vertical to that axis.

What we claim is:

1. A method for measuring an internal refractive index of an optical fiber preform from a state of bending of a light ray passing across the optical fiber preform, said method comprising:

scanning a surface of a light source by a knife-edge;

determining a light ray start position on the light source depending on an interception of the light ray by the knife-edge or a de-interception of the light ray; and determining a refractive index distribution of the optical fiber preform based on an angle of the bending of the light ray calculated from a relation between the light ray start position and a light ray detection position, wherein said optical fiber preform is situated parallel to said light source.

2. The method according to claim 1, further comprising:

phototaking the knife-edge passing across the optical fiber preform;

extracting a portion of the knife-edge image corresponding to the position of the section of the optical fiber preform to be measured, which is vertical to a specific axis thereof;

combining portions of the knife-edge image into one single image as a function of the knife-edge position or as a function of time when the knife-edge is scanned at a constant speed; and analyzing the combined image to determine the angle of the bending of the light ray from a geometrical relation between the light ray start position and the light ray detection position.

3. The method according to claim 1 or 2, wherein the light source is a self-emission type image display device;

and further comprising displaying a shape of the knife-edge on a screen of the display device as a scanning moving image.

4. The method according to claim 3, wherein the self-emission type image display device is a CRT or a liquid crystal display device having a backlight.

5. A system for measuring an internal refractive index of an optical fiber preform from a state of bending of a light ray passing across the optical fiber preform, in which a refractive index distribution of the optical fiber preform is determined based on an angle of the bending of the light ray calculated from a relation between start and detection positions of the light ray, said system comprising:

a planar light source;

a knife-edge for scanning the front surface of the planar light source in a direction vertical to the axis of the optical fiber preform;

a supporting device for supporting the optical fiber preform in front of the knife-edge;

a phototaking device for phototaking an image of the planar light source scanned through the optical fiber preform; and a processing device for calculating the angle of the bending of the light ray from a position at which the light ray is intercepted by the knife-edge or a position at which the light ray is de-intercepted and a corresponding position on the image pickup plane of the phototaking device, and finding the internal refractive index of the optical fiber preform based on the angle of bending.

6. The system according to claim 5, wherein the self-emission type image display device is a CRT or a liquid crystal display device having a backlight.

7. A system for measuring an internal refractive index of an optical fiber preform from a state of bending of a light ray passing across the optical fiber preform, in which a refractive index distribution of the optical fiber preform is determined based on the angle of the bending of the light ray calculated from a relation between start and detection positions of the light ray, said system comprising:

a self-emission type image display device for displaying a scanning moving image of knife-edge shape;

a supporting device for supporting the optical fiber preform in front of the image display device;

a phototaking device for phototaking the scanning moving image of knife-edge shape through the optical fiber preform;

and a processing device for calculating the angle of the bending of the light ray from a position at which the light ray is intercepted by the knife-edge or a position at which the light ray is de-intercepted and a corresponding position on the image pickup plane of the phototaking device, and finding the internal refractive index of the optical fiber preform based on the angle of bending.

* * * * *